(12) United States Patent
Adams et al.

(10) Patent No.: US 6,736,828 B1
(45) Date of Patent: May 18, 2004

(54) METHOD FOR PERFORMING ENDOLUMINAL FUNDOPLICATION AND APPARATUS FOR USE IN THE METHOD

(75) Inventors: Ronald D. Adams, Holliston, MA (US); Charles H. Pugsley, Jr., Pelham, NH (US)

(73) Assignee: SciMed Life Systems, Inc., Maple Grove, MN (US)

( * ) Notice: Subject to any disclaimer, the term of this patent is extended or adjusted under 35 U.S.C. 154(b) by 396 days.

(21) Appl. No.: 09/675,601

(22) Filed: Sep. 29, 2000

(51) Int. Cl.$^7$ ................................................ A61B 17/08
(52) U.S. Cl. ........................ 606/213; 606/151; 606/220
(58) Field of Search .......................... 606/153, 21–221, 606/205; 128/898; 600/104

(56) References Cited

U.S. PATENT DOCUMENTS

| | | | |
|---|---|---|---|
| 3,667,472 A | * 6/1972 | Halpern ....................... 606/214 |
| 5,088,979 A | 2/1992 | Filipi et al. |
| 5,403,326 A | 4/1995 | Harrison et al. |
| 5,458,575 A | 10/1995 | Wang |
| 5,558,665 A | 9/1996 | Kieturakis |
| 5,571,116 A | 11/1996 | Bolanos et al. |
| 6,067,990 A | * 5/2000 | Kieturakis ....................... 606/1 |
| 6,086,528 A | * 7/2000 | Adair ......................... 606/213 |
| 6,086,600 A | * 7/2000 | Kortenbach ................. 606/139 |
| 6,113,609 A | * 9/2000 | Adams ....................... 606/213 |
| 6,159,146 A | * 12/2000 | El Gazayerli ............... 606/219 |
| 6,312,437 B1 | * 11/2001 | Kortenbach ................. 606/219 |
| 6,387,437 B1 | * 5/2002 | Martinez-Bustos et al. . 426/622 |
| 2002/0156344 A1 | 10/2002 | Pasricha et al. ............ 600/113 |

OTHER PUBLICATIONS

Pentax Literature: Product Information.
Netter's Atlas of Human Anatomy, Plates 258 & 259.
Gastrointestinal Endoscopy, Copyright 1997, "A New Intraluminal Antigastroesophageal Reflux Procedure in Babons".
Annals of Surgerty, vol. 220. No. 4, 472–483, 1994 J. B. Lippincott Company, Laparoscopic Nissen Fundoplication Is An Effective Treatment for Gastroesophageal Reflux Disease.

\* cited by examiner

*Primary Examiner*—Michael J. Milano
*Assistant Examiner*—Jessica R Baxter
(74) *Attorney, Agent, or Firm*—Finnegan Henderson Farabow Garrett & Dunner, L.L.P.

(57) ABSTRACT

A method and device for performing endoluminal fundoplication are described. A device is inserted in the patient's stomach through the esophagus, including an unit adapted to grasp and pull a portion of the gastroesophageal junction into the stomach, and an unit adapted to move a portion of the fundus towards the esophagus. The device also can place fasteners to hold the gastric wall and the esophageal wall secured together, thus forming a valve between esophagus and stomach. An adhesive compound can be used to stabilize the juncture of the two walls.

23 Claims, 10 Drawing Sheets

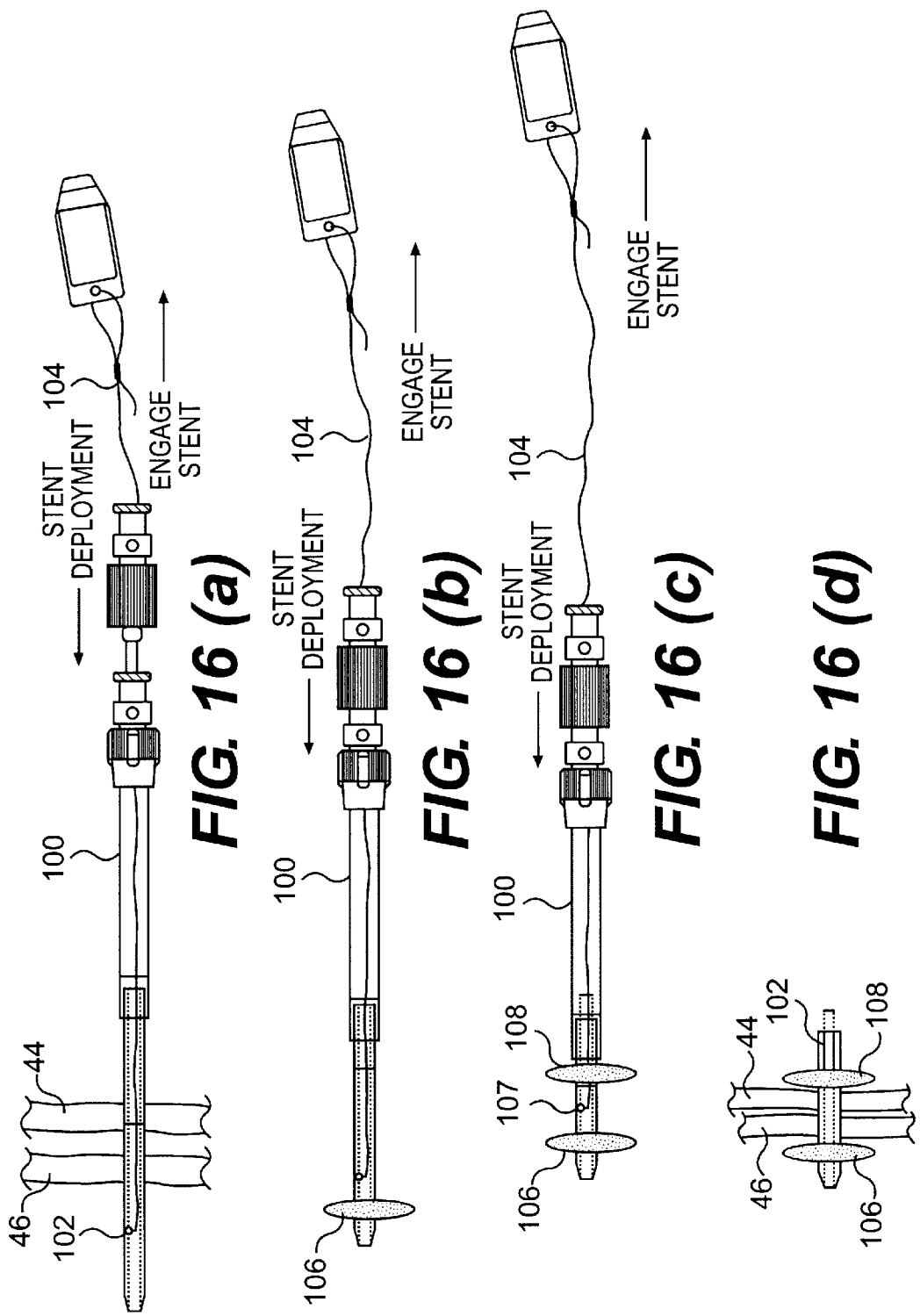

METHOD FOR PERFORMING ENDOLUMINAL FUNDOPLICATION AND APPARATUS FOR USE IN THE METHOD

FIELD OF THE INVENTION

The present invention relates generally to the art of fundoplicating the stomach to the esophagus. More specifically, the present invention relates to a method for performing such a fundoplication endoluminally, and to an apparatus for securing the fundus to the esophagus.

BACKGROUND OF THE INVENTION

Fundoplication is a surgical procedure which is typically used to treat Gastroesophageal Reflux (GER) condition, a malady often resulting from a deformity of the gastroesophageal junction (GEJ), and/or a dysfunctional lower esophageal sphincter (LES). One symptom commonly associated with GER is regurgitation or reflux of stomach contents into the esophagus. Fundoplication procedures are directed towards manipulating esophageal and gastric tissue so as to form a valve at the GEJ which limits reflux into the esophagus. The valve is formed by manipulation of the esophagus so as to invaginate the stomach, then wrapping the fundus of the stomach around the distal end of the esophagus and securing the stomach in that wrapped position.

The most commonly used fundoplication procedures require abdominal or thoracic incisions through which the abdominal wrapping and securing can be performed. Due to the highly invasive nature of such surgery, 2 complications and morbidity occur in a significant percentage of cases. In addition, these procedures are lengthy, often taking a number of hours to perform, and may leave disfiguring scars where the incisions were made.

Other recently developed fundoplication procedures somewhat limit the necessity of making large surgical incisions by utilizing laparoscopic ports or percutaneous endoscopic gastrostomy. (See, e.g. U.S. Pat. Nos. 5,403,326, and 5,088,979, the contents of which are hereby incorporated by reference). Although these procedures are less invasive than those involving large abdominal and thoracic incisions, they are invasive nonetheless, and have costs and risks associated with such invasive surgery. For example, general anaesthesia is typically used during these procedures which adds to the expense of these procedures and entails well known risks.

In addition to the complications, risks, and costs associated with the invasive nature of current fundoplication methods, these methods have other problems as well. One such problem is unwrapping of the fundus, also referred to as slippage of the fundal wrap. Slippage frequently occurs with current methods, as they fail to adequately secure the plicated fundus.

SUMMARY OF THE INVENTION

The present invention is directed to a method for endoluminal fundoplication in which a flexible endoscope is first used to locate an attachment site at the gastroesophageal junction. A tissue grasping device is then positioned at the distal end of the endoscope, and attached to the body tissue at the located attachment site. Next, a tissue displacement device is positioned at the distal end of the endoscope and used to displace the fundus of the stomach, so as to create an intussusception of the esophagus into the gastric lumen.

A fastener delivery device is then positioned adjacent to a first desired fastener delivery location and used to place a first fastener through the tissue which forms the intussusception at the desired fastener delivery location. The first fastener secures a first portion of the gastric fundus to the esophagus. The fastener delivery device is then used to place additional fasteners at a plurality of additional desired fastener locations, thus securing the gastric fundus around the esophagus. In one exemplary embodiment, the fastener delivery device, the tissue grasping device, and the tissue displacement device can be incorporated into a single unit.

Finally, an injection device is positioned at the distal end of the endoscope and used to inject a bonding agent into the tissue which forms the intussusception. For example, the bonding agent can be an agent for fibrotic fixation or adhesion.

In one embodiment, the invention is a method for performing endoluminal fundoplication of a patient's esophagus and stomach, having the steps of forming an intussusception of the esophagus into the stomach by pulling a selected portion of the esophagus into the stomach, and by displacing a fundus portion of the stomach towards the esophagus, placing a fastener across the intussusception, said fastener maintaining an esophageal wall and a gastric wall forming the intussusception adjacent to one another, and injecting a bonding agent between the esophageal wall and a gastric wall to bond the intussusception.

In another embodiment, the invention is a device for performing endoluminal fundoplication of a patient's esophagus and stomach, comprising a flexible tube having a distal end adapted for insertion in the stomach through the esophagus, a tissue grasping device disposed at the distal end of the flexible tube, adapted to grasp a selected portion of the esophagus, a tissue displacement device disposed adjacent the tissue grasping device, adapted to move a fundus portion of the stomach towards the esophagus and an anvil portion, pivotable relative the tissue displacement portion, wherein the tissue displacement device and the anvil portion releasably carry complementary portions of a fastener, such that said complementary portions are joined when the fundus portion is moved towards the esophagus.

BRIEF DESCRIPTION OF THE DRAWINGS

The invention will be more readily understood through the following detailed description, with reference to the accompanying drawings, in which:

FIG. 1 shows a cross-sectional view of the distal end of an esophagus and the upper gastric wall, with an endoscope inserted through the esophagus and into the gastric lumen, and a tissue grasping device attached to a site on the gastroesophageal junction;

FIG. 2 shows the cross-sectional view as in FIG. 1 and, in addition, shows a tissue displacement device and the gastric fundus displaced so as to form an intussusception of the esophagus into the gastric lumen;

FIG. 3 shows the cross-sectional view as in FIG. 2 and, in addition, shows a tissue fastener device and a fastener placed through the intussusception;

FIG. 4 shows a cross-sectional view of the distal end of an esophagus and the upper gastric wall, with an endoscope inserted through the esophagus and into the gastric lumen, two fasteners placed within the intussusception, and an injection device inserted into the intussusception;

FIGS. 16a, 16b, 16c and 16d are side views showing the deployment device for a fastener according to another embodiment of the present invention.

DETAILED DESCRIPTION OF THE INVENTION

Figure 3:
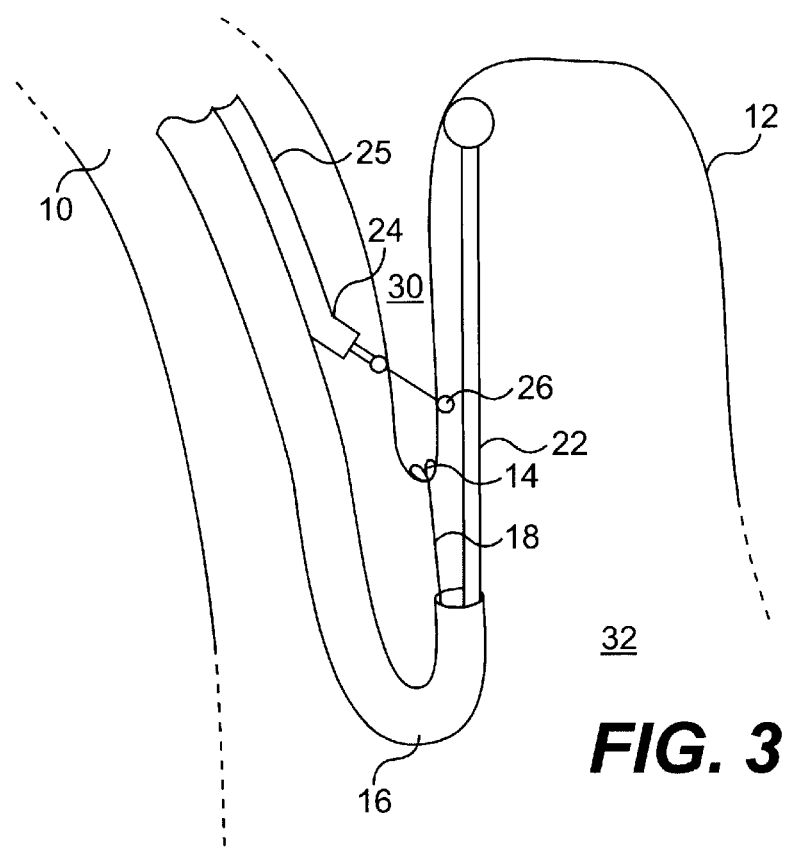
Figure 4:
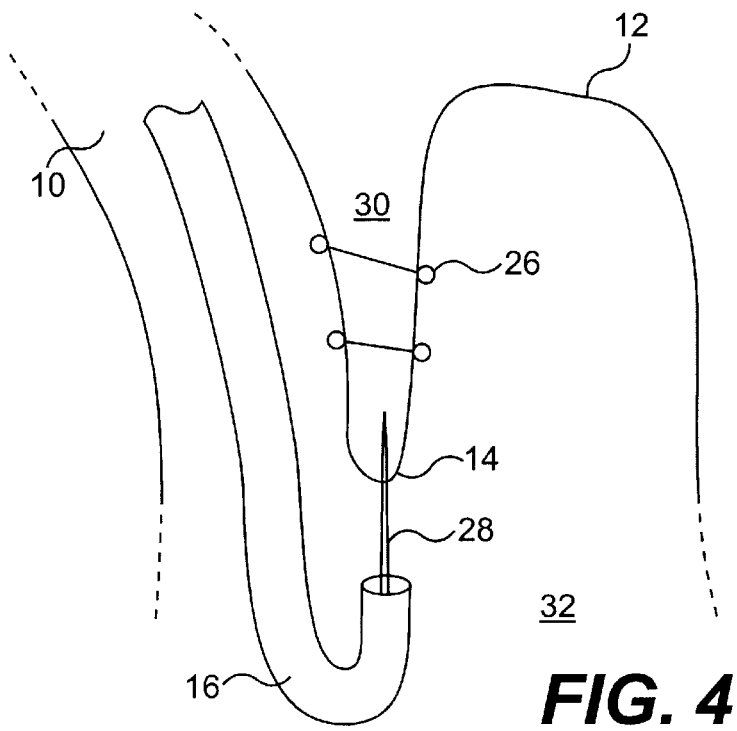

The method of the present invention can be performed, for example, using a flexible endoscope 16, which is preferably equipped with a tissue grasping device 18 (shown in FIG. 1), a tissue displacement device 22 (shown in FIG. 2), a fastener delivery device 24 (shown in FIG. 3), and an injection device 28 (shown in FIG. 4). The endoscope preferably has one or more oversheath channels through which various devices may pass. For example, the endoscope may be equipped with a tissue displacement device which passes through the lumen of an oversheath channel, and can be controllably extended past the distal end of the endoscope by the endoscopist. In addition, the endoscope preferably has a second oversheath channel through which a fastener delivery device passes and an injection device operable at its distal end. The endoscopist can operate the endoscope, including the tissue grasping device, tissue displacement device, fastener delivery device, and injection device from the proximal end of the endoscope.

Figure 15A:
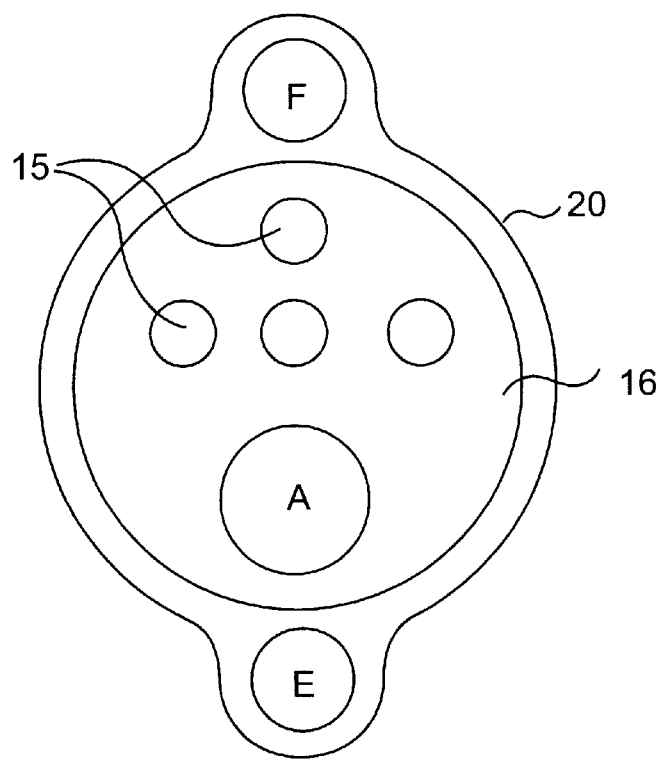
FIGS. 15a and 15b. are cross sectional views showing two embodiments of an endoscope, with one and two overtubes.
Figure 15B:
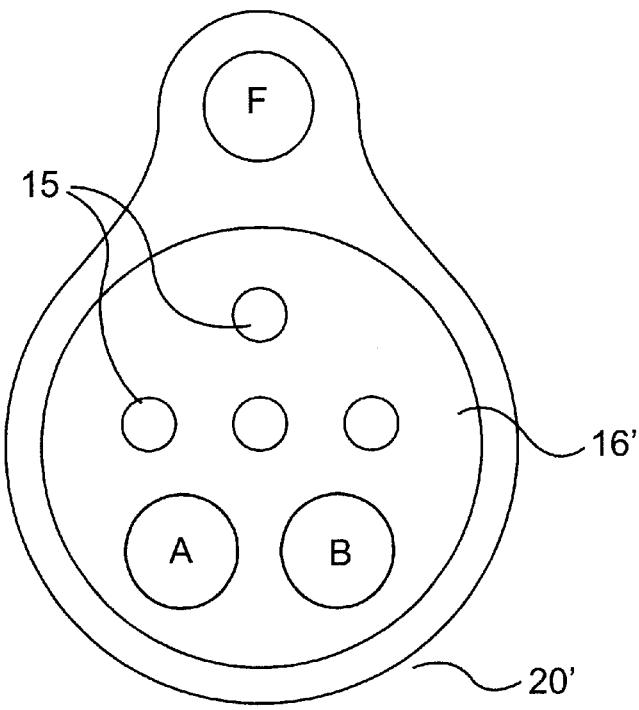

Different types of endoscopes can be used for this procedure. If necessary, an overtube with one or more passages can be slipped over the endoscope to the location of the fundoplication, to facilitate insertion of additional tools. For example, FIG. 15a shows an endoscope 16 having several channels 15 that provide irrigation, suction, illumination and video feedback. This exemplary endoscope 16 includes one working channel A. To facilitate insertion of additional tools, an overtube 20 can be used, forming a sheath that defines additional working channels E and F that reach the distal end of endoscope 16. Similarly, FIG. 15b shows an endoscope 16' having two working channels A and B. In this case, an overtube 20' only has to provide a passage for one additional working channel F. In this discussion, an "endoscopic device" is used to generally indicate and endoscope and, when required, an overtube defining additional working channels.

In one embodiment, the patient's stomach is insufflated to facilitate the operation. The patient can also be sedated with an intravenous anesthesia injection during the procedure.

Figure 1:
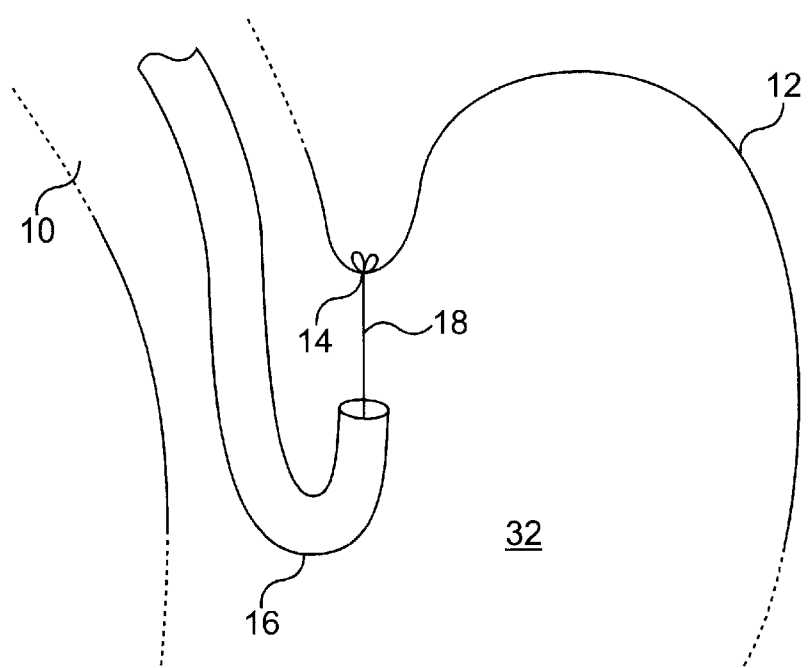
FIGS. 1 through 4 illustrate the method of endoluminal fundoplication according to one embodiment of the present invention.

Using the present method, the flexible endoscope 16 is first inserted into the patient's mouth, passed through the esophagus 10 and into the stomach, as shown in FIG. 1. The inserted endoscope 16 is then used to locate an attachment site 14 at the gastroesophageal junction. The endoscopist, or other practitioner performing the procedure, can locate the site by viewing the GEJ through the endoscope. These methods for endoscopically locating target sites are well known and widely used in the art.

The tissue grasping device 18 can be positioned at the located attachment site 14, and engaged so as to grasp and hold that tissue, as shown in FIG. 1. The tissue grasping device 18 passes through a lumen of the endoscope 16 and is operable from the proximal end of the endoscope 16 by the practitioner. Preferably, the practitioner can control the engaging/disengaging of the device 18, as well as the tension which the device 18 applies to the engaged tissue. This tension can be controlled by extending the device 18 past or retracting the device 18 towards the distal end of the endoscope 16. The means with which the tissue grasping device 18 engages, or grasps, and holds the tissue can consist of a hook, clamp, grasper, a combination thereof, or the like, as is known in the art.

Figure 2:
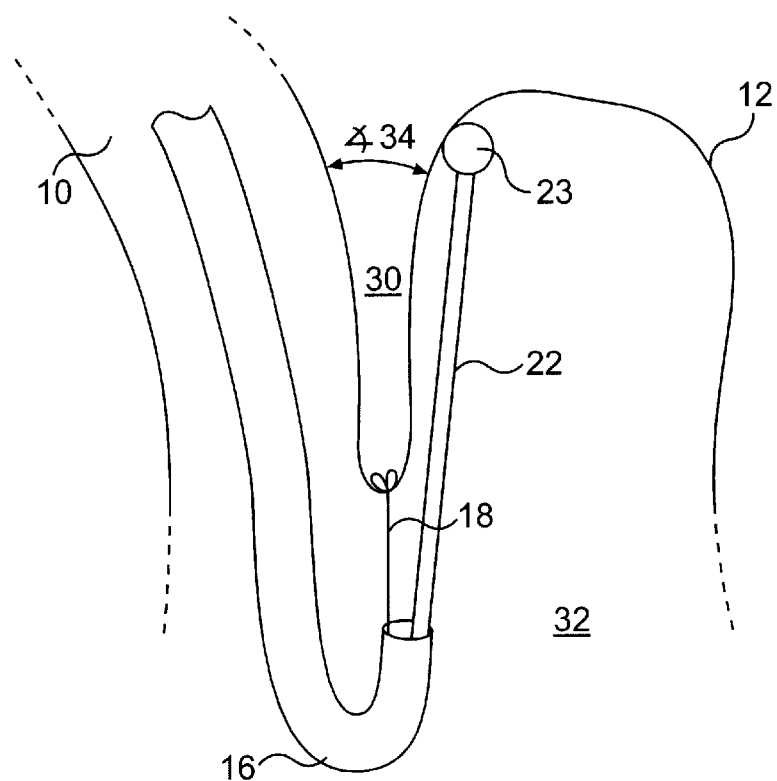

After tissue at the GEJ has been grasped, the tissue displacement device 22 is used to displace the gastric fundus 12 so as to effectively create an intussusception 30 of the esophagus 10 into the stomach 32, as shown in FIG. 2. The tissue displacement device 22 passes through a lumen of an overtube 20 which surrounds the endoscope 16, and can be pushed or rotated to a position distal to the distal tip of the endoscope 16. The device 22 preferably comprises a spherical tip 23 located at the distal end of a stiff cable or Nitinol band. The practitioner can operate the tissue displacement device 22, for example, by pushing and rotating it into position against the gastric fundus.

Once in position against the gastric fundus 12, the tissue displacement device 22 is further pushed and rotated so as to press against and reposition the gastric fundus 12. Simultaneously, the tissue grasping device 18 holds the tissue at the attachment site 14, applying a force which opposes force supplied by the tissue displacement device 22. The net effect of these counteracting forces is that the gastric fundus 12 is brought in closer proximity to the esophagus, which makes the angle of His, identified at reference numeral 34, more acute. The displacement of the gastric fundus 12 creates a tissue flap 30, which is effectively an intussusception of the esophagus 10 into the stomach 32. In one preferred embodiment, the flaps of tissue can have an approximate length between 1 and 3 cm.

In a preferred embodiment, the steps of pulling the tissue with the tissue grasping device 18 and displacing the fundus with the tissue displacement device 22 are repeated at several positions around the circumference of the intussusception. For example, the procedure can be performed at four to twelve equidistant locations around the circumference of the esophagus.

The reduction in the angle of His 34 and formation of an intussusception 30 reduces the degree to which stomach contents can reflux into the esophagus 10. A valve is essentially built between the stomach and the esophagus. As gases build up in the gastric lumen 32 and, more specifically, in the gastric fundus 12, pressure is brought to bear on the wrapped portion of the esophagus 10, closing it off from the stomach. In addition, stomach contents move around within the gastric lumen 32 due to contraction of the stomach muscles, and body movement in general. The intussusception 30 alleviates GER by creating a valve like barrier which stomach contents must pass through in order to reach the esophagus 10.

The intussuscepted esophagus 30 is then fastened to the wall of the gastric fundus 12 to fix the arrangement. The fastener delivery device 24 is used to insert fasteners 26 within the intussusception 30 to hold the gastric and esophageal tissue in place. Since a number of nerves and blood vessels typically run through the tissue being manipulated, the practitioner should, before inserting the fasteners 26, locate the nerves and blood vessels, so as not to damage or sever them. In particular, the practitioner should locate the Vagus nerve bundle which runs alongside the esophagus, the aorta, and the various gastric blood vessels. Numerous methods for locating such anatomical features are well known in the art, including use of ultrasound, fluoroscopy and x-ray.

Once the aforementioned features are located, the practitioner loads a fastener 26 into the fastener delivery device 24 and inserts the device 24 through a second sheath channel 25 until the operating end of the delivery device 24 is positioned at a desired fastener insertion site. The device 24 is then used to place a fastener at a desired site, as shown in FIG. 3. Fasteners 26 are preferably inserted through the intussusception at 1cm and 2.5 cm above the tip 14 of the newly-formed tissue flap 30, which extends into the gastric lumen 32. The fasteners 26 can be inserted also at other locations along the length of the tissue flap, which in the preferred case has a length of between about 1 and 3 cm.

The fastener delivery device 24 can be rotated within the esophagus and gastric lumen so as to insert fasteners around the entire circumference of the esophagus. Preferably, fasteners are inserted at locations approximately 30° apart. For example, from an initial insertion site, the device 24 may be rotated in one direction, inserting fasteners at 30°, 60°, 120°, and 180° from the initial site. The device 24 is then returned to the initial insertion site and rotated in the opposite direction, again inserting fasteners at, for example, 30° intervals, until the entire circumference of the intussusception has been fastened.

Preferably, the intussusception should extend a full 360 degrees, i.e., the entire circumference of the esophagus. The valve formed by the intussusception is similar to the "gerd standard" open or laparosopic procedure, a Nissen Fundoplication. However, a full 360 degrees may not be achievable with an endoluminal approach. In that case, a Toupet fundoplication, spanning approximately 270 degrees of the circumference around the esophagus can be performed. The endoluminal procedure thus cannot generally be performed on an arc of approximately 60 degrees, on the back side of the esophagus. In the remaining portion of the esophagus circumference, fasteners can be attached, for example, at 30 degrees intervals.

Figure 5:
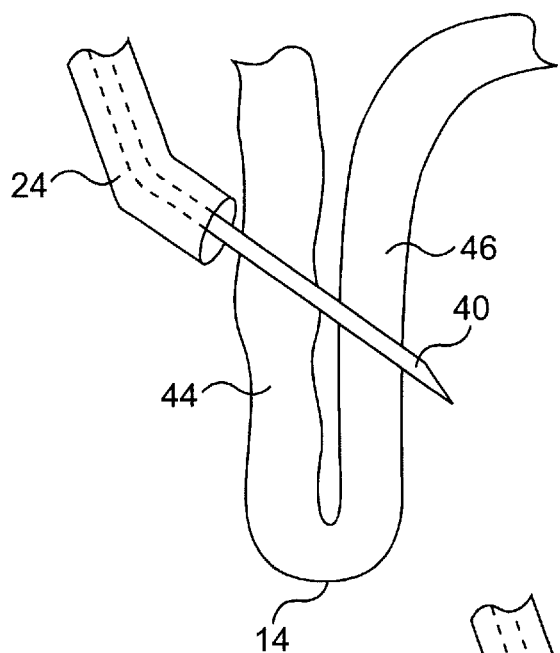
FIG. 5 shows a cross-sectional view of an intussusception of the esophagus into the gastric lumen with a hypotube inserted through both the esophageal and gastric walls.

FIG. 5 shows a hypotube 40 with a beveled edge which has been inserted through the fastener delivery device 24 and further advanced so as to penetrate tissue of both the esophageal and gastric walls, 44 and 46 respectively. Hypotube 40 can be, for example, an hypodermic needle cannula, or another type of thin tubing, preferably of stainless steel.

Figure 6:
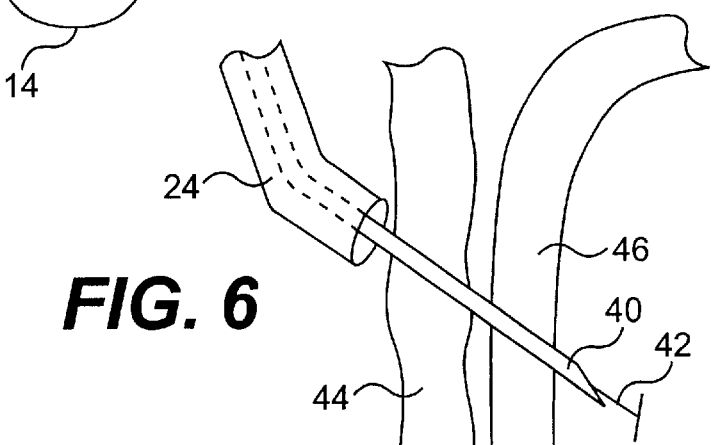
FIG. 6 shows the cross-sectional view as in FIG. 5, with the distal end of a T-fastener deployed.
Figure 7:
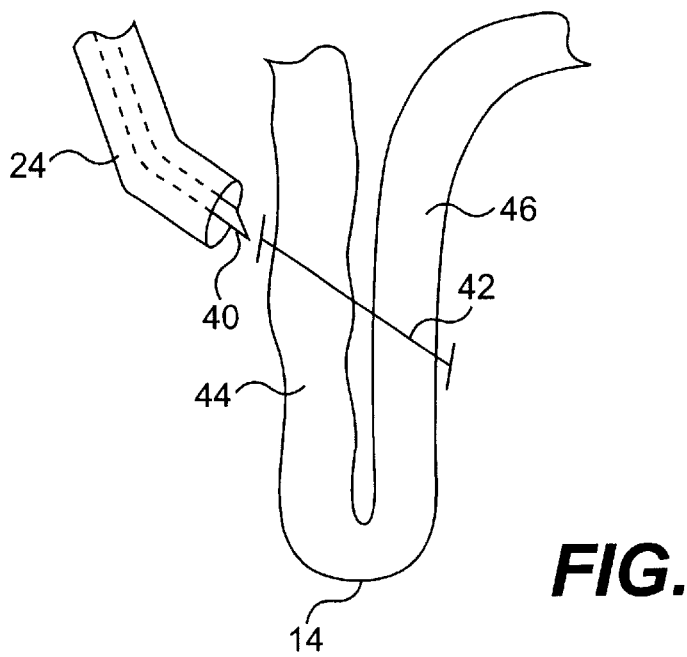
FIG. 7 shows the cross-sectional view as in FIG. 5, with the hypotube retracted from within the body tissue, and with both the proximal and distal ends of the T-fastener deployed.

A T-fastener 42 of the type known in the art can be inserted through the hypotube 40 until the distal end of the fastener 42 is deployed on the stomach side of the intussusception. The hypotube 40 is then retracted towards the sheath 24 so that the deployed distal end of the T-fastener engages the gastric wall 46 as the hypotube 40 is retracted, as shown in FIG. 6. As shown in FIG. 7, the hypotube 40 is further retracted into the sheath 24 until the proximal end of the T-fastener is pulled out of the hypotube 40 by the tension exerted from the distal end of the T-fastener 42. The proximal end of the T-fastener 42 then seats against the inner wall of the esophagus, thereby holding the gastric wall and the esophagus together. The length of the longitudinal center portion of the T-fastener determines the maximum distance between the inner wall of the esophagus and the inner wall of the fundus.

Figure 8:
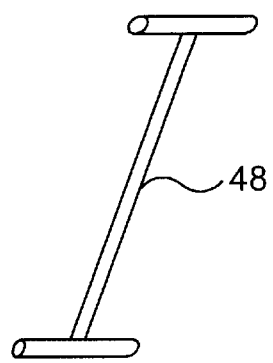
FIG. 8 shows an elevation view of a T-fastener with a T-bar bolster at each end.

FIGS. 8–11 illustrate various configurations of T-fasteners which may be used to secure the esophageal and gastric walls. The traditional T-fastener 48 has a simple T-bar at each end, as shown in FIG. 8. With this fastener, the forces of securing the gastric and esophageal tissue in the post-deformation position are borne by the T-bars at each end of the fastener, which have a small area over which to distribute the forces. This type of T-bar may pull through either the gastric or esophageal wall. Thus, it may be desirable to utilize T-fasteners in conjunction with the present invention which have T-bar configurations with increased area over which the forces of securing the tissue will be distributed.

Figure 9:
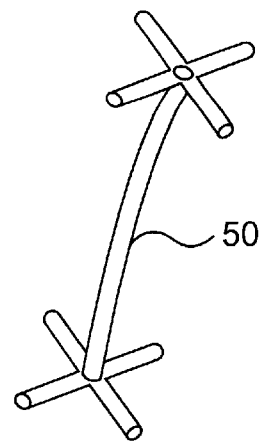
FIG. 9 shows an elevation view of a fastener with a four-pronged bolster at each end.
Figure 10:
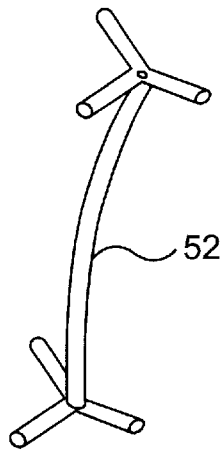
FIG. 10 shows an elevation view of a fastener with a three-pronged bolster at each end.
Figure 11:
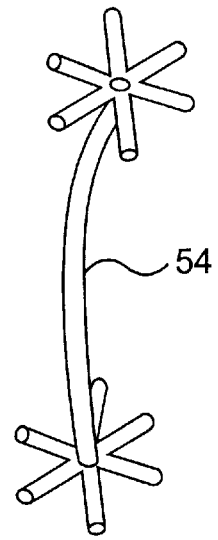
FIG. 11 shows an elevation view of a fastener with a six-pronged bolster at each end, in which the prongs are curved.

FIG. 9 shows a T-fastener with two T-bar bolster at each end. In addition, the area over which the forces of securing tissue are distributed can be increased by, for example, utilizing a T-fastener with three prongs, four prongs, or six prongs. (Shown in FIGS. 10, 9, and 11 respectively.)

Figure 12:
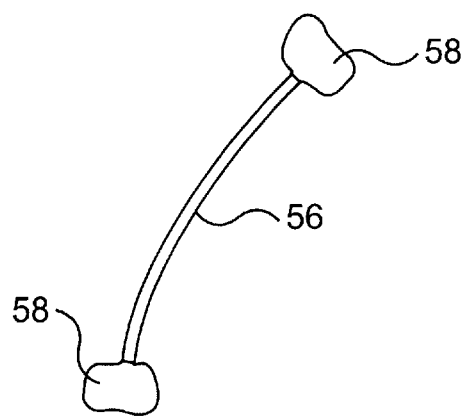
FIG. 12 shows an elevation view of a fastener with inflatable bolsters on each end.

FIG. 12 shows an alternative fastener 56 which can be used to secure gastric and esophageal tissue according to the present invention. The fastener 56 has a longitudinal center portion with inflatable balloons 58 at each end. This fastener 56 may be inserted through the gastric and esophageal tissue in the same manner as that described above with respect to T-fastener insertion. Once the fastener 56 is in place, air, water or other material may be introduced into the inflatable ends 58, thereby inflating the ends 58 and securing the gastric and esophageal tissue. The inflatable ends may be spherical or disk-shaped.

In one exemplary embodiment, the balloon can be formed on the distal end of fastener 42, as shown in FIG. 12, and can be stored in hypotube 40 during insertion through walls 44, 46. As hypotube 40 is retracted, the balloon can be inflated with a fluid passing through an inflation tube formed within hypotube 40. A similar process can take place to inflate a balloon at the proximal end of fastener 42, before separation from hypotube 40. Seals of known design can be used to maintain both balloons inflated.

Figure 13A:
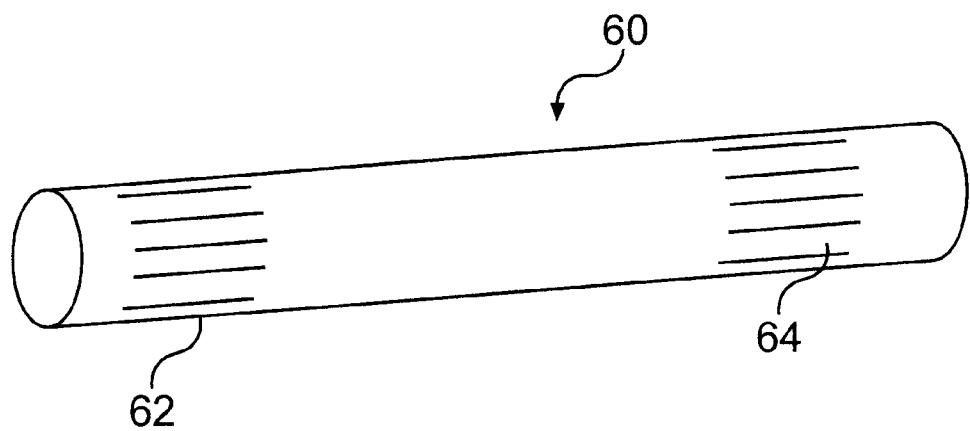
FIG. 13a. is a longitudinal view of a fastener with deformable portions near each end, with the fastener in the undeformed position.
Figure 13B:
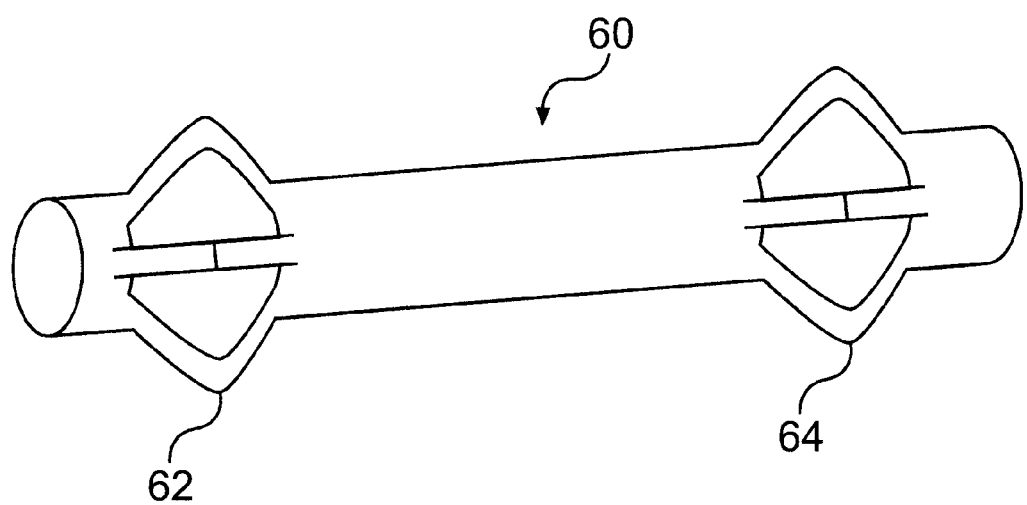
FIG. 13b is a longitudinal view of the fastener shown in FIG. 13a, with the deformable portions near each end in the deformed position.

FIGS. 13*a*–13*b* show yet another alternative fastener 60 which may be uused to secure gastric and esophageal tissue according to the present invention. The fastener 60 is a longitudinal member with deformable portions 62, 64 near the proximal and distal ends, and may preferably be made of polypropylene or other biocompatible durable material.

The deformable portions 62, 64 preferably have a mesh-like structure which may be expanded radially by, for example, buckling when the ends of the fastener 60 are compressed toward on another. The fastener 60 is inserted into the gastric and esophageal tissue in the same manner as described above with respect to T-fastener insertion, as shown in FIGS. 5–7. When the proximal and distal ends are in desired positions within the esophagus and the stomach respectively, the ends are expanded.

In one exemplary embodiment, the fastener 60 may be formed such that it is normally biased toward the deformed position, as shown in FIG. 13b. A fastener 60 of this type can be maintained in the reduced diameter configuration while contained within in the hypotube 40, and would expand due to its natural bias upon release therefrom. The deformable portions 62 and 64 are compressed so as to allow insertion of the fastener through the delivery device 24 and through both gastric and esophageal tissue. The fastener 60 can then be advanced through the hypotube 40 until the distal deformable portion 64 exits the distal end of the hypotube 40, and regains its normally radially expanded position. The hypotube 40 can then be retracted, allowing the proximal deformable portion 62 to expand to its normally radially expanded position. The deformed portions 62 and 64 then act as bolsters which secure the gastric and esophageal tissue in place.

Alternatively, a fastener 60 with deformable portions 60 may be formed such that it is normally in the un-deformed position, as shown in FIG. 13a. The normally un-deformed fastener would be inserted through the gastric and esophageal tissue in the same manner as described above with respect to the normally deformed embodiment. The normally un-deformed fastener must then be manipulated into the deformed position shown in FIG. 13b after being placed in the desired position spanning the esophageal and stomach tissue. A crimping device, inserted through the lumen of the endoscope, can be used to perform such manipulation. This device may resemble a known mechanism used for inserting rivets. As would be understood by those skilled in the art, any device which may be inserted through the lumen of an endoscope and which can compress the ends of the fastener 60 so as to buckle the deformable portions may be used as the crimping device.

The fastener 60 may also be formed with a needle-like point at its distal end to aid insertion. Such a distal end would enable insertion of the fastener 60 directly through the gastric and esophageal tissue, eliminating the need for the hypotube 40.

As shown in FIG. 16, the hypotube 40 previously described with reference to FIGS. 5–7 can be replaced with an insertion device 100 that deploys a fastener 102. When insertion device 100 is in position across the esophageal and gastric walls 44, 46, as shown in FIG. 16a, an actuating wire 104 that extends the length of endoscope 16 is pulled, so that a distal stent 106 is deployed, as seen in FIG. 16b. As the insertion device 100 is withdrawn, actuating wire 104 is pulled again as shown in FIG. 16c, so that proximal stent 108 is deployed, and the walls 44, 46 are sandwiched between stents 106, 108, as shown in FIG. 16d.

Figure 14:
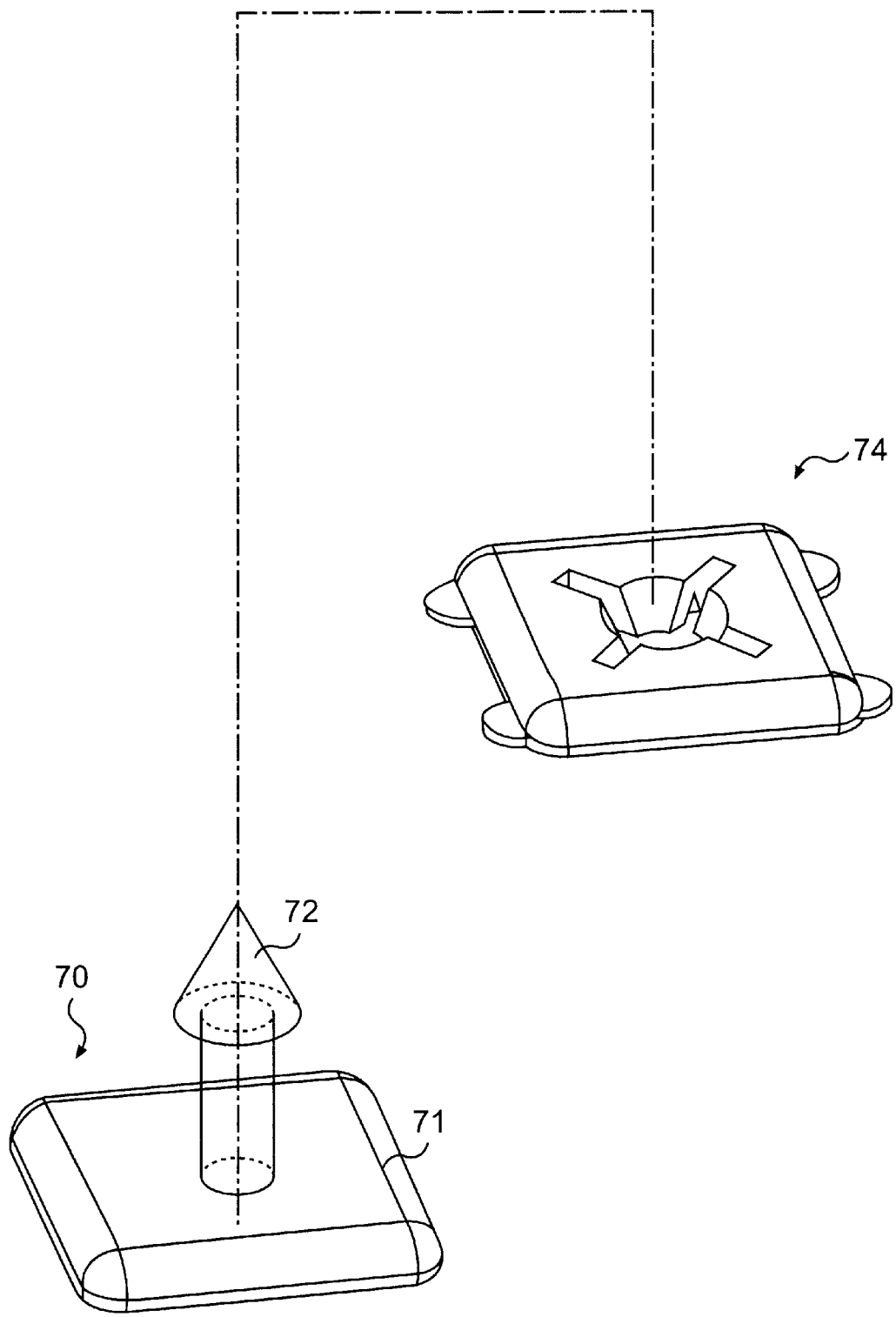
FIG. 14 is an isometric drawing showing another embodiment of a fastener according to the invention, having a portion with a barbed tack, and another portion with a mating washer.

In a different embodiment according to the invention, a two-piece fastener comprising a barbed tack 70 and a mating washer 74, as shown in FIG. 14, may be employed. The barbed tack 70 consists of a disk portion 71 with a barbed connector 72. The barbed connector 72 can be inserted through the mating washer 74 such that the connector 72 is engaged by the washer 74. Both components 70 and 74 can preferentially be made of a resilient polymeric material.

Figure 17A:
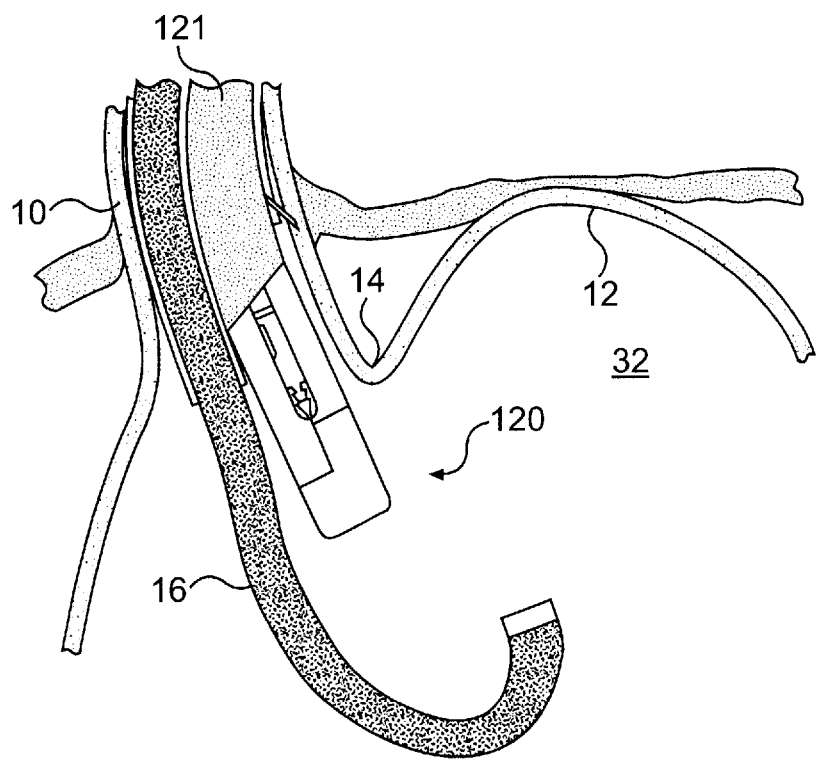
FIGS. 17a to 17e are diagrams showing the steps of operation of a different embodiment of a system according to the present invention, which includes a fundoplication device.
Figure 17B:
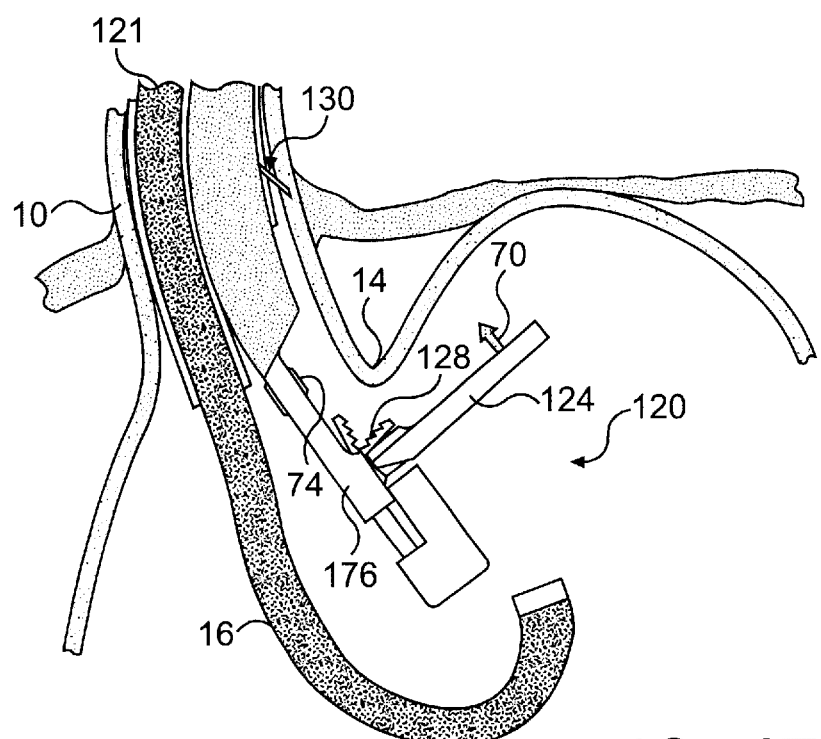

In one alternative exemplary embodiment of a device according to the invention, the barbed tack 70 and mating washer 74 may be inserted using a fundoplication device 120, that is described in FIGS. 17a to 17e. FIG. 17a shows a device 120 at the end of a flexible tube 121, that is inserted through esophagus 10 into the patient's stomach 32. An endoscope 16 can also be introduced, to visually monitor the procedure. Once in position, device 120 deploys a pivotable tissue displacing portion 124, shown in FIG. 17b, that is moved in position towards the gastric fundus 12.

Figure 17C:
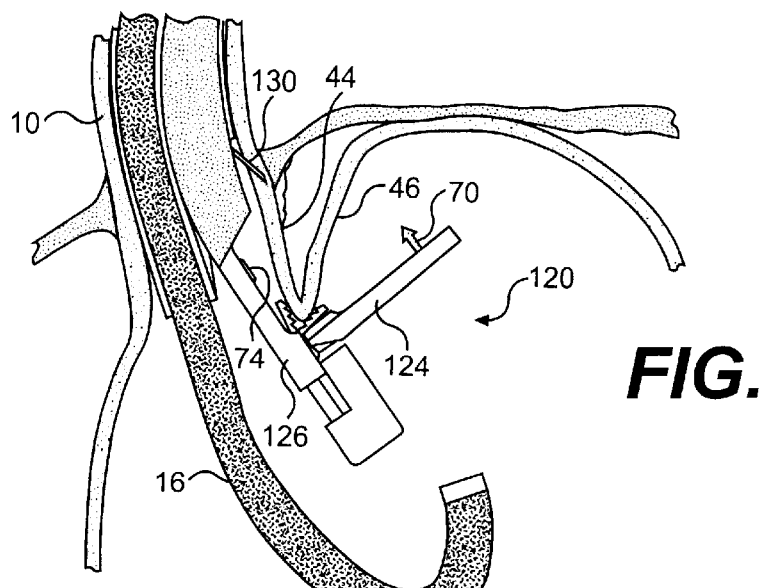

A gripping portion 128 of device 120 is used to grasp an attachment site 14 at the gastroesophageal junction, as shown in FIG. 17c, so that downward movement of device 120 pulls that region of the esophagus 10 into stomach 32. A spike 130 can also be used to facilitate this procedure. Once the esophagus opening is in the proper position, tissue displacement portion 124 is pivoted towards an anvil portion 126 of the device 120, so that fundus 12 is pushed towards the esophagus, forming an intussusception.

Figure 17D:
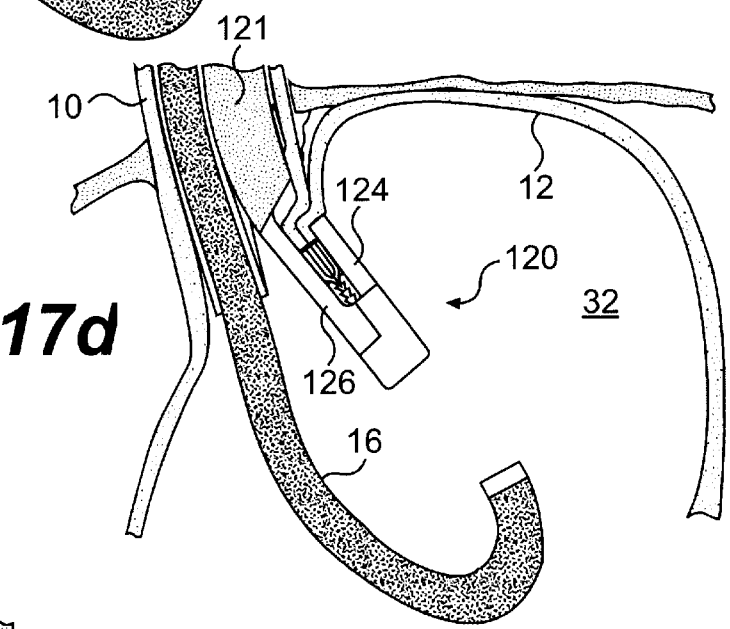
Figure 17E:
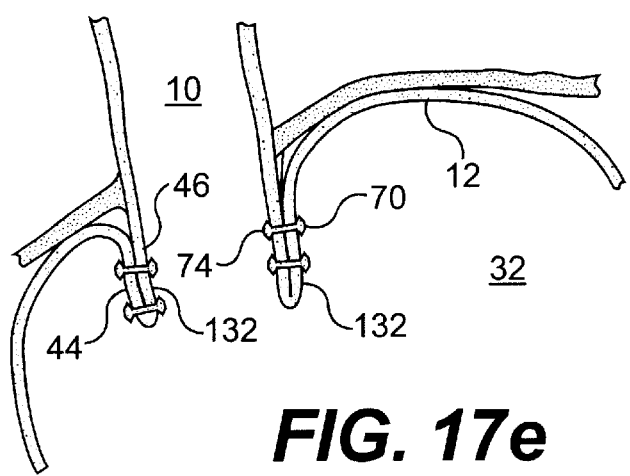

When tissue displacement portion 124 reaches anvil portion 126, as shown in FIG. 17d, the barbed portion 70 of the fastener, mounted on tissue displacement portion 124, pierces the gastric wall 46 and esophageal wall 44, and is secured to mating washer 74, mounted on anvil portion 126. This procedure results in formation of a flap of tissue 132. As previously discussed for other embodiments according to the invention, this procedure can be repeated at different circumferential locations around the esophagus, to form a valve of desired shape separating stomach 32 from esophagus 10, as shown in FIG. 17e.

Finally, a bonding agent can be injected into the tissue of the intussusception, as shown in FIG. 4, causing a fibrotic reaction which secures the gastric and esophageal tissue of the fundoplication. Sodium morrhuate, for example, is a known agent that may be injected into the tissue fold formed between the gastric and esophageal tissue, so as to create a fibrotic reaction that adheres the gastric fundus to the esophagus permanently.

Several compounds can be used as bonding agents. For example, among the adhesive compounds, cyanoacrylate can be used, as well as fibrin sealant, muscle adhesive protein, Transforming Growth Factor Beta, Prolamine gel, Gelatin-Resorcinol-Formol glue and Hystoacryl. Among the sclerosant compounds, Morrhuate Sodium, Sodium Tetradecyl Sulfate, Ethanolamine Oleate, aerosol-tale and sterile Bleomycin Sulfate can be used.

When such a bonding agent is used, the fastener need only secure the tissue until the reaction caused by the agent has sufficiently secured the tissue in place. The fastener used may then be made of a biodegradable or bioabsorbable material, or can be removed.

What is claimed is:

1. A method for performing endoluminal fundoplication of a patient's esophagus and stomach, comprising:

introducing an endoscopic device through the patient's esophagus, the endoscopic device comprising an endoscope, a tissue displacement device, and a fastener delivery device;

forming an intussusception of the esophagus into the stomach by pressing against a fundus portion of the stomach towards the esophagus with the tissue displacement device;

placing a fastener across the intussusception with the fastener delivery device after the step of forming the intussusception so as to maintain an esophageal wall and a gastric wall adjacent to one another; and injecting a bonding agent between the esophageal wall and the gastric wall.

2. The method according to claim 1, wherein the step of forming the intussusception further comprises pulling a selected portion of the esophagus into the stomach.

3. The method according to claim 2, wherein the step of pulling the selected portion of the esophagus into the stomach is performed by a grasping device, the grasping device being configured to extend from the endoscopic device and grasp and pull the selected portion of the esophagus into the stomach.

4. The method according to claim 1, further comprising removing the fastener after bonding the intussusception.

5. The method according to claim 1, further comprising extending the tissue displacement device from the endoscopic device.

6. The method according to claim 1, further comprising:
   introducing through the esophagus and positioning the fastener delivery device adjacent to the intussusception at a desired fastening location; and
   delivering the fastener from the fastener delivery device for placing the fastener across the intussusception.

7. The method according to claim 6, further comprising; extending a hypotube from the fastener delivery device across the intussusception;
   deploying a distal end of the fastener from the hypotube onto one of the stomach and esophageal sides;
   withdrawing the hypotube from the intussusception; and
   deploying a proximate end of the fastener onto the other of the stomach and esophageal sides to maintain the esophageal wall and the gastric wall adjacent to one another.

8. The method according to claim 7, wherein the deploying steps further comprise inflating bladders disposed at at least one of the distal and proximate ends of the fastener.

9. The method according to claim 8, further comprising successively positioning the fastener delivery device and delivering the fastener at selected positions around a circumference of the intussusception.

10. The method according to claim 7, wherein the deploying steps further comprise extending a deformable portion disposed at at least one of the distal and proximate ends of the fastener.

11. The method according to claim 6, further comprising repeating the positioning and delivering steps a selected number of times.

12. The method according to claim 1, further comprising extending from the endoscopic device the fastener delivery device for placing the fastener across the intussusception.

13. The method according to claim 1, wherein the injecting step further comprises injecting at least one of an adhesive and a sclerosant agent.

14. The method according to claim 1, wherein the tissue displacement device further comprises an anvil portion and a tissue displacing it portion pivotally coupled to the anvil portion, and wherein pressing against the fundus portion includes pivotally moving the tissue displacing portion with respect to the anvil portion of the tissue displacement device, such that the gastric wall and the esophageal wall are positioned between the anvil portion and the tissue displacing portion.

15. A method for performing endoluminal fundoplication of a patient's body, comprising:
   inserting an endoscopic device through a patient's esophagus, the endoscopic device comprising an endoscope, a tissue displacement device, and a fastening device;
   positioning the endoscopic device adjacent the gastroesophageal junction;
   grasping a selected portion of the esophageal wall;
   pressing a fundus wall of the stomach towards the esophageal wall with the tissue displacement device; and
   inserting a fastener through the esophageal wall and the fundus wall with the fastening device, after pressing the fundus wall of the stomach towards the esophageal wall.

16. The method according to claim 15, further comprising injecting one of an adhesive agent and a sclerosant agent between the fundus wall and the esophageal wall.

17. The method according to claim 15, wherein the endoscopic device further comprises a grasping device, wherein the step of grasping the selected portion of the esophageal wall is performed with the grasping device.

18. The method according to claim 15, wherein the endoscopic device includes an overtube having at least one channel for accommodating at least one of the endoscope and the tissue displacement device.

19. The method according to claim 15, further comprising rotating the fastening device about an axis of the esophagus by a selected rotational angle and repeating the step of deploying the fastener.

20. The method according to claim 19, wherein the rotating step comprises rotating the fastening device by about 30 degrees.

21. The method according to claim 15, further comprising removing the fastener after bonding of the fundus wall to the esophageal wall.

22. The method according to claim 15, further comprising pulling the grasped selected portion of the esophagus into the stomach.

23. The method according to claim 15, further comprising;
   extending a hypotube from the fastening device across the esophageal wall and the fundus wall;
   deploying a distal end of the fastener from the hypotube onto one of stomach and esophageal sides;
   withdrawing the hypotube from the esophageal wall and the fundus wall; and
   deploying a proximate end of the fastener onto the other of the stomach and esophageal sides to maintain the esophageal wall and the fundus wall adjacent to one another.

* * * * *

UNITED STATES PATENT AND TRADEMARK OFFICE
CERTIFICATE OF CORRECTION

PATENT NO.   : 6,736,828 B1  
DATED        : May 18, 2004  
INVENTOR(S)  : Ronald D. Adams et al.

It is certified that error appears in the above-identified patent and that said Letters Patent is hereby corrected as shown below:

Title page,
Item [*] Notice, "396 days" should read -- 246 days --.

Signed and Sealed this

Twentieth Day of July, 2004

JON W. DUDAS
*Acting Director of the United States Patent and Trademark Office*